(12) United States Patent
Abt et al.

(10) Patent No.: US 9,757,536 B2
(45) Date of Patent: Sep. 12, 2017

(54) SOFT TIP CANNULA

(75) Inventors: Niels A. Abt, Winterthur (CH); Hans Jürg Wehrli, Schaffhausen (CH); Heiko Kromer, Schaffhausen (CH)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 13/619,369

(22) Filed: Sep. 14, 2012

(65) Prior Publication Data

US 2014/0025045 A1    Jan. 23, 2014

Related U.S. Application Data

(60) Provisional application No. 61/672,550, filed on Jul. 17, 2012.

(51) Int. Cl.
*A61M 25/00* (2006.01)
*A61M 1/00* (2006.01)
(Continued)

(52) U.S. Cl.
CPC ....... *A61M 25/001* (2013.01); *A61B 17/3421* (2013.01); *A61F 9/007* (2013.01); *A61M 1/008* (2013.01); *A61M 1/0084* (2013.01); *A61M 1/0086* (2014.02); *A61M 25/0069* (2013.01); *B29C 65/48* (2013.01); *B29C 65/70* (2013.01); *B29C 66/02241* (2013.01); *B29C 66/2272* (2013.01); *B29C 66/5344* (2013.01); *B29C 70/766* (2013.01); *A61B 17/3417* (2013.01); *A61B 2017/00964* (2013.01); *A61B 2017/3454* (2013.01); *A61B 2090/08021* (2016.02);
(Continued)

(58) Field of Classification Search
CPC ............................................ A61M 2025/0081
See application file for complete search history.

(56) References Cited

U.S. PATENT DOCUMENTS 268,996 A     12/1882  Brinkerhoff
2,525,329 A *  10/1950  Wyzenbeek .................. 604/267
(Continued)

FOREIGN PATENT DOCUMENTS

CN       102186423        9/2011
DE          651436       10/1937
(Continued)

OTHER PUBLICATIONS

The Free Dictionary, Saunders Comprehensive Veterinary Dictionary 3rd Ed., Definition of French Gauge, 2007.*
(Continued)

*Primary Examiner* — Lynsey Eiseman
*Assistant Examiner* — Manolis Pahakis

(57) ABSTRACT

The present disclosure describes numerous example medical instruments that include an elongated portion having a proximal end and a distal end, and a passage defined therethrough and a soft tip coupled to the distal end of the elongated portion. The tip may be formed from a soft material. In some instances, the soft material may have a hardness less than the material forming the elongated portion. The tip may also include a passage that may be of a substantially equivalent size as the passage of the elongated portion. The tip may be coupled to the distal end of the elongated portion at an engagement site having a surface area greater than a cross-sectional area of the elongated portion.

8 Claims, 10 Drawing Sheets

(51) Int. Cl.

| | |
|---|---|
| *A61F 9/007* | (2006.01) |
| *B29C 65/48* | (2006.01) |
| *B29C 70/76* | (2006.01) |
| *B29C 65/00* | (2006.01) |
| *B29C 65/70* | (2006.01) |
| *A61B 17/00* | (2006.01) |
| *A61B 17/34* | (2006.01) |
| *B29L 23/00* | (2006.01) |
| *B29C 65/56* | (2006.01) |
| *B29C 65/02* | (2006.01) |
| *A61B 90/00* | (2016.01) |
| *B29L 31/00* | (2006.01) |

(52) U.S. Cl.
CPC ............. *A61M 2025/0081* (2013.01); *A61M 2210/0612* (2013.01); *B29C 65/02* (2013.01); *B29C 65/56* (2013.01); *B29C 66/1142* (2013.01); *B29C 66/2274* (2013.01); *B29C 66/71* (2013.01); *B29K 2995/0056* (2013.01); *B29L 2023/007* (2013.01); *B29L 2031/7548* (2013.01); *Y10T 156/1066* (2015.01)

(56) References Cited

U.S. PATENT DOCUMENTS

| | | | | |
|---|---|---|---|---|
| 2,677,373 | A * | 5/1954 | Barradas | 604/192 |
| 2,697,437 | A | 12/1954 | Everett | |
| 3,203,285 | A * | 8/1965 | Schmidt | B25G 1/025 29/425 |
| 3,230,949 | A * | 1/1966 | Rodriguez-Olleros | 600/565 |
| 3,433,226 | A * | 3/1969 | Boyd | 606/159 |
| 3,470,867 | A * | 10/1969 | Goldsmith | A61B 10/0283 600/566 |
| 3,547,103 | A * | 12/1970 | Cook | A61M 25/0152 600/585 |
| 3,589,363 | A | 6/1971 | Banko et al. | |
| 3,659,607 | A | 5/1972 | Banko | |
| 3,844,272 | A | 10/1974 | Banko | |
| 3,865,666 | A * | 2/1975 | Shoney | 156/245 |
| 3,908,637 | A * | 9/1975 | Doroshow | 600/573 |
| 3,976,070 | A | 8/1976 | Dumont | |
| 4,221,220 | A * | 9/1980 | Hansen | 604/119 |
| 4,362,520 | A * | 12/1982 | Perry | F16D 3/18 464/149 |
| 4,380,998 | A * | 4/1983 | Kieffer et al. | 600/200 |
| 4,445,890 | A | 5/1984 | Patel | |
| 4,449,539 | A * | 5/1984 | Sarstedt | 600/577 |
| 4,490,138 | A * | 12/1984 | Lipsky et al. | 604/40 |
| 4,530,356 | A | 7/1985 | Helfgott et al. | |
| 4,531,943 | A * | 7/1985 | Van Tassel | A61M 25/0069 600/435 |
| 4,551,292 | A * | 11/1985 | Fletcher | A61M 25/001 264/139 |
| 4,706,659 | A * | 11/1987 | Matthews | A61B 17/164 464/173 |
| 4,842,590 | A * | 6/1989 | Tanabe et al. | 604/524 |
| 4,900,300 | A | 2/1990 | Lee | |
| 4,921,483 | A * | 5/1990 | Wijay et al. | 604/103.1 |
| 5,003,989 | A * | 4/1991 | Taylor et al. | 600/585 |
| 5,047,008 | A | 9/1991 | de Juan, Jr. et al. | |
| 5,078,702 | A * | 1/1992 | Pomeranz | 604/524 |
| 5,092,848 | A * | 3/1992 | deCiutiis | 604/170.01 |
| 5,135,481 | A | 8/1992 | Nemeh | |
| 5,139,504 | A | 8/1992 | Zelman | |
| 5,203,595 | A * | 4/1993 | Borzone | A61B 17/1631 285/325 |
| 5,217,465 | A | 6/1993 | Steppe | |
| 5,234,416 | A * | 8/1993 | Macaulay et al. | 604/527 |
| 5,312,356 | A * | 5/1994 | Engelson et al. | 604/164.13 |
| 5,320,635 | A * | 6/1994 | Smith | A61B 17/32002 408/713 |
| 5,329,923 | A * | 7/1994 | Lundquist | 600/373 |
| 5,330,501 | A * | 7/1994 | Tovey et al. | 606/198 |
| 5,374,252 | A | 12/1994 | Banks et al. | |
| 5,385,561 | A | 1/1995 | Cerny | |
| 5,441,496 | A * | 8/1995 | Easley et al. | 606/15 |
| 5,445,624 | A | 8/1995 | Jimenez | |
| 5,454,378 | A * | 10/1995 | Palmer et al. | 600/564 |
| D364,456 | S * | 11/1995 | Solnit et al. | D24/112 |
| 5,487,725 | A | 1/1996 | Peyman | |
| 5,509,910 | A * | 4/1996 | Lunn | 604/525 |
| 5,514,086 | A | 5/1996 | Parisi et al. | |
| 5,533,988 | A * | 7/1996 | Dickerson et al. | 604/523 |
| 5,545,153 | A | 8/1996 | Grinblat et al. | |
| 5,562,691 | A | 10/1996 | Tano et al. | |
| 5,569,218 | A * | 10/1996 | Berg | 604/525 |
| 5,584,821 | A * | 12/1996 | Hobbs et al. | 604/524 |
| 5,593,402 | A | 1/1997 | Patrick | |
| 5,651,783 | A | 7/1997 | Reynard | |
| 5,656,011 | A * | 8/1997 | Uihlein et al. | 600/146 |
| 5,700,252 | A * | 12/1997 | Klingenstein | 604/525 |
| 5,716,363 | A | 2/1998 | Josephberg | |
| 5,738,677 | A | 4/1998 | Colvard et al. | |
| 5,762,637 | A * | 6/1998 | Berg et al. | 604/264 |
| 5,807,241 | A * | 9/1998 | Heimberger | 600/142 |
| 5,811,043 | A * | 9/1998 | Horrigan et al. | 264/138 |
| 5,814,010 | A | 9/1998 | Ziegler | |
| 5,850,496 | A | 12/1998 | Bellahsene et al. | |
| 5,860,963 | A * | 1/1999 | Azam et al. | 604/528 |
| 5,921,970 | A * | 7/1999 | Vandenberg | 604/264 |
| 5,938,635 | A * | 8/1999 | Kuhle | A61M 5/3286 604/272 |
| 5,989,262 | A | 11/1999 | Josephberg | |
| 6,007,478 | A * | 12/1999 | Siess et al. | 600/16 |
| 6,015,391 | A * | 1/2000 | Rishton et al. | 600/567 |
| 6,033,375 | A | 3/2000 | Brumbach | |
| 6,053,922 | A * | 4/2000 | Krause | A61B 17/164 464/78 |
| 6,059,792 | A | 5/2000 | Josephberg | |
| 6,129,762 | A * | 10/2000 | Li | 623/13.11 |
| 6,251,134 | B1 * | 6/2001 | Alt et al. | 623/1.16 |
| 6,273,876 | B1 * | 8/2001 | Klima et al. | 604/264 |
| 6,273,882 | B1 * | 8/2001 | Whittier et al. | 606/1 |
| 6,292,701 | B1 * | 9/2001 | Prass et al. | 607/116 |
| 6,325,790 | B1 * | 12/2001 | Trotta | 604/523 |
| 6,375,648 | B1 | 4/2002 | Edelman et al. | |
| 6,491,670 | B1 | 12/2002 | Toth et al. | |
| 6,500,157 | B2 * | 12/2002 | Luther | 604/264 |
| 6,575,934 | B2 * | 6/2003 | Duchamp | A61M 25/1034 604/102.02 |
| 6,610,005 | B1 * | 8/2003 | Tao | 600/34 |
| 6,641,564 | B1 | 11/2003 | Kraus | |
| 6,682,493 | B2 * | 1/2004 | Mirigian | 600/585 |
| 6,800,076 | B2 | 10/2004 | Humayun | |
| 6,849,068 | B1 | 2/2005 | Bagaoisan et al. | |
| 6,902,558 | B2 | 6/2005 | Laks | |
| 6,916,314 | B2 | 7/2005 | Schneider et al. | |
| 6,921,397 | B2 * | 7/2005 | Corcoran et al. | 604/535 |
| 6,964,750 | B2 * | 11/2005 | Fulford | 264/328.8 |
| 6,979,328 | B2 | 12/2005 | Baerveldt et al. | |
| 7,077,823 | B2 * | 7/2006 | McDaniel | 604/95.01 |
| 7,077,848 | B1 | 7/2006 | de Juan, Jr. et al. | |
| 7,207,980 | B2 | 4/2007 | Christian et al. | |
| 7,217,263 | B2 | 5/2007 | Humayun et al. | |
| 7,285,107 | B1 * | 10/2007 | Charles | 604/35 |
| 7,297,142 | B2 * | 11/2007 | Brock | 606/1 |
| 7,384,407 | B2 * | 6/2008 | Rodriguez et al. | 604/22 |
| 7,389,148 | B1 * | 6/2008 | Morgan | 607/116 |
| 7,413,563 | B2 * | 8/2008 | Corcoran et al. | 604/523 |
| 7,470,269 | B2 | 12/2008 | Auld et al. | |
| 7,485,113 | B2 | 2/2009 | Varner et al. | |
| 7,537,593 | B2 | 5/2009 | Humayun | |
| 7,549,972 | B2 | 6/2009 | Luloh et al. | |
| 7,691,087 | B2 | 4/2010 | Gough et al. | |
| 7,749,196 | B2 | 7/2010 | Osborne et al. | |
| 7,766,904 | B2 | 8/2010 | McGowan, Sr. et al. | |
| 7,785,321 | B2 | 8/2010 | Baerveldt et al. | |
| 7,819,887 | B2 * | 10/2010 | McGuckin et al. | 606/159 |
| 7,846,128 | B2 | 12/2010 | Venturelli | |
| 7,909,816 | B2 | 3/2011 | Buzawa | |
| 7,959,641 | B2 | 6/2011 | Sorensen et al. | |

(56) References Cited

U.S. PATENT DOCUMENTS

| | | | |
|---|---|---|---|
| 8,048,058 B2* | 11/2011 | Fulford | 604/523 |
| 8,057,500 B2* | 11/2011 | Mitusina | A61B 17/32002 |
| | | | 606/170 |
| 8,083,728 B2* | 12/2011 | Rome | 604/533 |
| 8,177,777 B2 | 5/2012 | Humayun | |
| 8,202,277 B2 | 6/2012 | Ryan | |
| 8,287,539 B2* | 10/2012 | Nelson et al. | 606/62 |
| 8,308,737 B2 | 11/2012 | Ryan | |
| 8,357,140 B2* | 1/2013 | Majercak et al. | 604/523 |
| 8,382,742 B2* | 2/2013 | Hermann | A61B 17/1631 |
| | | | 606/1 |
| 8,480,669 B2* | 7/2013 | Pappone et al. | 606/41 |
| 1,125,887 A1 | 1/2015 | Schimmel | |
| 2002/0002362 A1 | 1/2002 | Humayun et al. | |
| 2002/0035347 A1 | 3/2002 | Bagaoisan et al. | |
| 2002/0052641 A1* | 5/2002 | Monroe et al. | 623/1.11 |
| 2003/0028127 A1 | 2/2003 | Balzum et al. | |
| 2004/0015215 A1* | 1/2004 | Fredricks et al. | 607/96 |
| 2004/0030319 A1* | 2/2004 | Korkor | A61M 25/0662 |
| | | | 604/506 |
| 2004/0186484 A1 | 9/2004 | Ryan | |
| 2004/0254450 A1* | 12/2004 | Griffin et al. | 600/411 |
| 2005/0004523 A1 | 1/2005 | Osborne et al. | |
| 2005/0021046 A1 | 1/2005 | Bilge | |
| 2005/0033237 A1* | 2/2005 | Fentress et al. | 604/165.03 |
| 2005/0033309 A1 | 2/2005 | Ryan | |
| 2005/0038411 A1* | 2/2005 | Okada | A61L 29/049 |
| | | | 604/523 |
| 2005/0080400 A1* | 4/2005 | Corcoran | A61B 17/0057 |
| | | | 604/523 |
| 2005/0154379 A1 | 7/2005 | McGowan, Sr. et al. | |
| 2005/0209618 A1 | 9/2005 | Auld | |
| 2006/0106370 A1 | 5/2006 | Baerveldt et al. | |
| 2006/0127158 A1* | 6/2006 | Olson et al. | 401/53 |
| 2006/0149194 A1 | 7/2006 | Conston et al. | |
| 2006/0281566 A1* | 12/2006 | Lee | 464/149 |
| 2007/0078359 A1 | 4/2007 | Luloh et al. | |
| 2007/0106300 A1 | 5/2007 | Auld et al. | |
| 2007/0179471 A1 | 8/2007 | Christian et al. | |
| 2007/0265516 A1* | 11/2007 | Wang | 600/374 |
| 2007/0276420 A1 | 11/2007 | Sorensen et al. | |
| 2007/0282367 A1* | 12/2007 | Jeffrey | A61F 2/958 |
| | | | 606/194 |
| 2008/0021399 A1 | 1/2008 | Spaide | |
| 2008/0058761 A1* | 3/2008 | Spaide | 604/521 |
| 2008/0154204 A1 | 6/2008 | Varner et al. | |
| 2008/0161845 A1 | 7/2008 | Murakami et al. | |
| 2008/0207992 A1 | 8/2008 | Scheller et al. | |
| 2008/0275428 A1* | 11/2008 | Tegg et al. | 604/533 |
| 2008/0281294 A1 | 11/2008 | Forsberg | |
| 2009/0012517 A1* | 1/2009 | de la Rama et al. | 606/41 |
| 2009/0054872 A1* | 2/2009 | Magnuson | 604/523 |
| 2009/0099554 A1* | 4/2009 | Forster | A61F 2/2427 |
| | | | 606/1 |
| 2009/0234274 A1 | 9/2009 | Luloh et al. | |
| 2009/0287165 A1 | 11/2009 | Drapeau et al. | |
| 2009/0318856 A1 | 12/2009 | Glaser | |
| 2010/0010468 A1* | 1/2010 | Becker | 604/506 |
| 2010/0076271 A1 | 3/2010 | Humayun | |
| 2010/0089528 A1* | 4/2010 | Morris et al. | 156/245 |
| 2010/0100045 A1 | 4/2010 | Pravongviengkham et al. | |
| 2010/0174162 A1 | 7/2010 | Gough et al. | |
| 2010/0305519 A1 | 12/2010 | McKinnon et al. | |
| 2011/0015675 A1* | 1/2011 | Howard | A61B 17/0401 |
| | | | 606/232 |
| 2011/0118582 A1* | 5/2011 | De la Rama et al. | 600/374 |
| 2011/0208114 A1 | 8/2011 | Morlet | |
| 2011/0288392 A1* | 11/2011 | de la Rama et al. | 600/374 |
| 2012/0010602 A1 | 1/2012 | Ryan | |
| 2012/0238946 A1* | 9/2012 | Nita et al. | 604/22 |
| 2012/0259353 A1* | 10/2012 | Houser et al. | 606/169 |

FOREIGN PATENT DOCUMENTS

| | | | |
|---|---|---|---|
| DE | 2104353 | 1/1971 | |
| EP | 0542246 A1 * | 5/1993 | A61M 25/001 |
| EP | 1504870 A2 | 2/2005 | |
| EP | 1578281 | 9/2005 | |
| EP | 1782781 | 5/2007 | |
| EP | 1615604 | 8/2009 | |
| GB | 456458 | 11/1936 | |
| GB | 1238086 | 7/1971 | |
| GB | 1448129 | 9/1976 | |
| JP | 4303116 B | 7/2005 | |
| JP | 2006507100 | 3/2006 | |
| JP | 3779819 | 5/2006 | |
| JP | 2007514465 | 6/2007 | |
| JP | 5255041 | 8/2013 | |
| JP | 2013244186 | 12/2013 | |
| JP | 2014100558 | 6/2014 | |
| JP | 2014140711 | 8/2014 | |
| JP | 2014147612 | 8/2014 | |
| RU | 90684 U1 | 1/2010 | |
| SU | 1456109 | 2/1989 | |
| WO | 9208406 | 5/1992 | |
| WO | 98/25542 A2 | 6/1998 | |
| WO | 0113805 | 3/2001 | |
| WO | 0115640 | 3/2001 | |
| WO | 0168016 | 9/2001 | |
| WO | 03000312 | 1/2003 | |
| WO | 03045290 | 6/2003 | |
| WO | 2004047651 | 6/2004 | |
| WO | 2004093761 | 11/2004 | |
| WO | 2008011225 | 1/2008 | |
| WO | 2013/137208 A1 | 9/2013 | |
| WO | 2014/084355 A1 | 6/2014 | |

OTHER PUBLICATIONS

CareFusion Corporation, Soft tissue biopsy needles, Brochure, 2010.*

Smith & Nephew Inc., Trucath Spinal Injection System, Advanced technology for transforaminal injections, 2009.*

International Search Report and Written Opinion of the International Searching Authority, International Application No. PCT/US2013/048867, dated Oct. 22, 2013, 7 pages.

Page out of Grieshaber Switzerland Catalog, Aug. 1998, 1 page.

Page out of Alcon, Inc. Catalog, Oct. 2010, 1 page.

A Simple Extrusion Needle with Flexible Cannula Tip for Vitreoretinal Microsurgery, Flynn, Jr., et al., American Journal of Ophthalmology, Feb. 1988, vol. 105, No. 2, pp. 215-216.

Applications of a Cannulated Extrusion Needle During Vitreoretinal Microsurgery, Flynn, Jr., et al., Retina, 1988, vol. 8, No. 1, pp. 42-49.

EP13820547.1; Supplementary European Search Report, dated May 21, 2015, 6 pgs.

Ashraf M. El-Batarny, MD, "Transconjunctival Sutureless 23-gauge Vitrectomy for Vitreoretinal Diseases: Outcome of 30 Consecutive Cases," Middle East Journal of Ophthalmology, Jul.-Dec. 2008, pp. 99-105, vol. 15, No. 3-4.

Grieshaber, Single-Use Accessories Catalog, 2011, 2 pages.

C. Kanawati et al., "EN Bloc' Dissection of Epimacular Membranes Using Aspiration Delamination," Royal College of Ophthalmologists, (1996), pp. 47-52.

Alcon, Inc., file history for "Surgical Probe," European Publication No. 1782781, Published May 9, 2007, 56 pages.

Alcon catalog, "Grieshaber Advanced Backflush DSP Coming Soon!," Sep. 21, 2010, 2 pages.

Auld, file history for "Rigid Shafted Instrumentation for Vitreoretinal Surgery," U.S. Appl. No. 11/070,788, filed Mar. 2, 2005, 80 pages.

Auld, file history for "Surgical Probe," U.S. Publication No. 2007/0106300, Published May 10, 2007, 237 pages.

Avci et al., "A New Surgical Approach for Indocyanine Green-Assisted Internal Limiting Membrane Peeling," Ophthalmic Surgery, Lasers & Imaging, Jul./Aug. 2004, vol. 25, No. 4, pp. 292-297, 6 pages.

(56) References Cited

OTHER PUBLICATIONS

Bausch & Lomb, "Single Use Catalog," 2010, 33 pages.
Devgan, "Adopting Refractive IOLs in a Cataract Practice," Cataract & Refractive Surgery Today, Apr. 2007, 3 pages.
Devgan, "Silicone-Coated Soft I/A Tip," Cataract & Refractive Surgery Today Europe, 2007, 4 pages.
El-Batarny, "Transconjunctival Sutureless 23-gauge Vitrectomy for Vitreoretinal Diseases: Outcome of 30 Consecutive Cases," Middle East Journal of Opthalmology, Jul.-Dec. 2008, vol. 15, No. 3-4, 7 pages.
Fine et al., "Bimanual Microincision Phaco," CRST Europe, 2007, 10 pages.
Flynn et al., "Design Features and Surgical Use of a Cannulated Extrusion Needle," Graefe's Arch Clin Exp Ophthalmol, 1989, 227:304-308.
Grieshaber DSP Backflush catalog, 2008, 1 page.
Grieshaber DSP Single Use Accessories catalog, Dec. 2011, 2 pages.
Kanawati et al., "'En Bloc' Dissection of Epimacular Membranes Using Aspiration Delamination," Eye, 1996, 10, pp. 47-52.
Letters to Editor, British Journal of Ophthalmology, Mar. 1992, 76(3), p. 191.
Letters to Editor, Retina, The Journal of Retinal and Vitreous Diseases, 1988, vol. 8, No. 3, pp. 221-222.
McCuen et al., "An Automated Aspirating-Backflush System for Fluid-Gas Exchange and Retinal Manipulation," Arch Ophthalmol, Jun. 1989, vol. 107, 1 page.
McLeod et al., "Modified Charles Flute Needle," British Journal of Ophthalmology, 1981, 65, p. 69.
Medical Tube Technology, Inc., "Hypodermic Needle Gauge Chart," Copyright 2004, http://www.medtube.com/hypo_chrt.htm, last visited Sep. 15, 2016, 2 pages.
Ohji et al., "A Stiffer and Safer Light Pipe for 25-Gauge Vitrectomy," Arch Ophthalmol, Oct. 2007, vol. 125, No. 10, 2 pages.
Oshima, "27-Gauge Vitrectomy," Retina Today, Apr. 2009, pp. 47-49.
Oshima, et al., "Self-Retaining 27-Gauge Transconjunctival Chandelier Endoillumination for Panoramic Viewing During Vitreous Surgery," American Journal of Ophthalmology, Jan. 2007, vol. 143, No. 1, 3 pages.
Peyman, "A Combination Pick and Flute Needle," Arch Ophthalmol, Nov. 1989, vol. 107, 1 page.
Pravongviengkham, file history for "Trocar Cannula with Atraumatic Tip," U.S. Publication No. 2010/0100045, Published Apr. 22, 2010, 440 pages.
Ryan, file history for "Small Gauge Surgical Instrument with Support Device," Application No. 10767556, Filed Jan. 29, 2004, 94 pages.
Ryan, file history for "Small Gauge Surgical Instrument with Support Device," Application No. 10844592, Filed May 12, 2004, 170 pages.
Scheller et al., file history for "Microsurgical Illuminator with Adjustable Illumination," U.S. Publication No. 2008/0207992, Published Aug. 28, 2008, 75 pages.
Varner, file history for "Method and Device for Subretinal Drug Delivery," U.S. Publication No. 2008/0154204, Published Jun. 26, 2008, 47 pages.
Varner, file history for "Method for Drug Delivery Through the Vitreous Humor," U.S. Pat. No. 7,485,113, Issued Feb. 3, 2009, 408 pages.
Williams, "25-, 23-, or 20-gauge Instrumentation for Vitreous Surgery?," Eye, 2008, pp. 1-4.
Williams, "27-Gauge Twinlight Chandelier Illumination System for Bimanual Transconjunctival Vitrectomy," The Journal of Retinal and Vitreous Diseases, Mar. 2008, vol. 28, Issue 3, pp. 518-519.
Williams, "New Technique for Inserting 27-Gauge Twinlight Chandelier Illumination Fibers into the Eye Using Intravenous Cannula," The Journal of Retinal and Vitreous Diseases, Jul.-Aug. 2009, vol. 29, Issue 7, pp. 1040-1042.
Zivojnovic et al., "A Brush Back-Flush Needle," Arch Ophthalmol, May 1988, vol. 106, 1 page.
Zivojnovic et al., "A Modified Flute Needle," American Journal of Ophthalmology, Oct. 1983, vol. 96, No. 4, 1 page.
PCT International Preliminary Report on Patentability and Written Opinion of the International Searching Authority, Application No. PCT/US2007/085444, dated May 26, 2009, 10 pages.

* cited by examiner

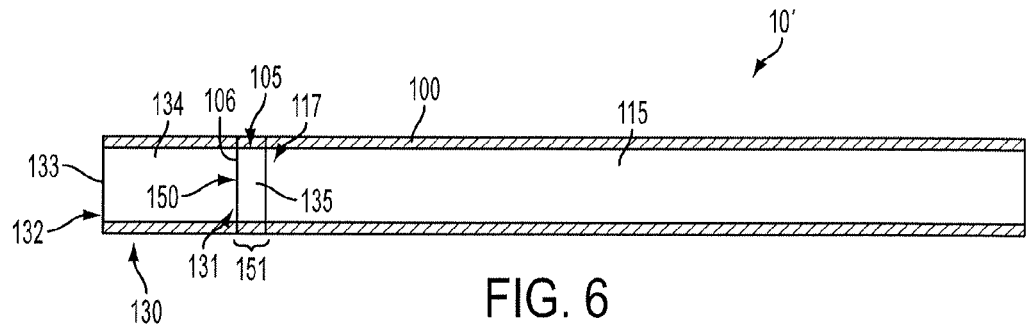
FIG. 6
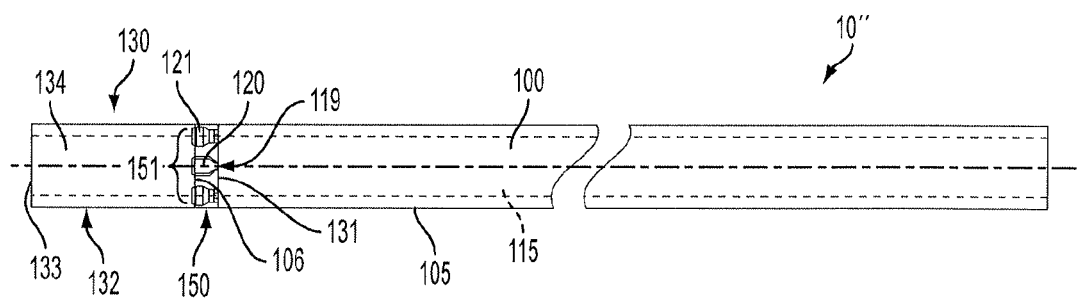
FIG. 7A
FIG. 7B

SOFT TIP CANNULA

CROSS-REFERENCE TO RELATED APPLICATIONS

This application claims the benefit of U.S. Provisional Application No. 61/672,550, filed Jul. 17, 2012, the entire contents of which are incorporated herein by reference

TECHNICAL FIELD

This disclosure relates generally to medical instruments. In particular, the disclosure relates to a cannula having a soft tip for ophthalmic procedures.

BACKGROUND

Cannulas are used in ophthalmic surgical procedures, such as retinal detachment surgery, to aspirate materials such as fluids including blood, aqueous humor, and infused balanced saline solutions. For ophthalmic surgical procedures, it is important that the instrument tip be designed to prevent or avoid damage to the eye tissue in the event of physical contact with the eye.

SUMMARY

According to one aspect, the disclosure relates to a medical instrument including an elongated portion having a distal end and a first passage and a tip coupled to the distal end of the elongated portion at an engagement site. The tip may include a second passage substantially equivalent in size to the first passage of the elongated portion. The engagement site may have a surface area greater than a cross-sectional area of the elongated portion.

Another aspect is directed to a method of forming a medical instrument including preparing a distal end of an elongated portion for attachment of a soft tip. Preparing the distal end may include laser cutting, water jet cutting, milling, drilling, a combination thereof, or any other suitable manufacturing method. The method may also include attaching a tip to the distal end of elongated portion. Attaching the tip may include molding, injection molding, insert molding, extrusion, adhering, a combination thereof, or any other suitable joining technique.

The various aspects may include one or more of the following features. The engagement site may include a tongue and groove connection. The tongue and groove connection may include at least one tongue formed on one of the elongated portion or the tip and at least one groove formed on the other of the elongated portion or the tip. The at least one tongue and the at least one groove may be interlocked with each other. The engagement site may include an enhanced surface. The tip may be molded to the enhanced surface. The elongated portion may include a needle or a cannula. The elongated portion may have a gauge size of 25 or less (e.g., 26 gauge, 27 gauge, or smaller gauge size). The passage of the tip may be tapered. The passage of the tip may taper from a smaller cross-sectional opening at a proximal end of the tip to a larger cross-sectional opening at a distal end of the tip. A distal end of the tip may be outwardly flared.

The tip may be formed from an elastomeric material. At least a portion of the tip may be formed from silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), polybenzimidazol (PBI), rubber, latex, combinations thereof, or other polymer or plastic compounds.

The details of one or more implementations of the present disclosure are set forth in the accompanying drawings and the description below. Other features, objects, and advantages will be apparent from the description and drawings, and from the claims.

BRIEF DESCRIPTION OF THE DRAWINGS

FIG. 6 is a cross-sectional view of another example instrument having a soft tip.

FIG. 7A is a side view of a further example instrument having a soft tip.

FIG. 7B is a detail view of an end of the cannula of FIG. 3A shows an engagement site between the soft tip and an elongated portion of the instrument.

Figure 1A:
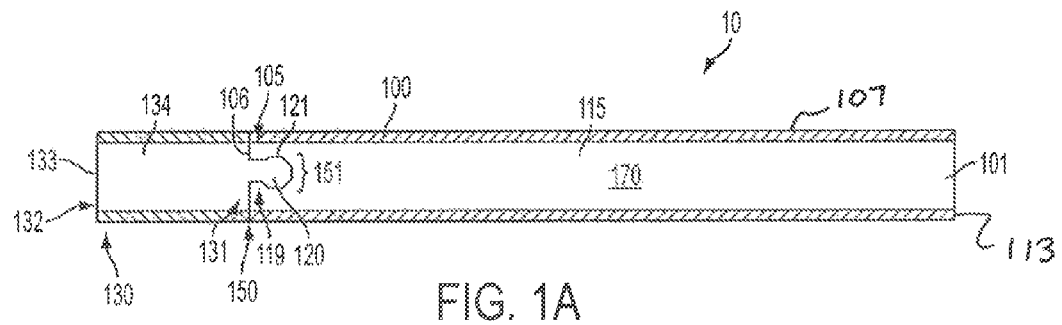
FIGS. 1A-1D show views of an example instrument having a soft tip.

Those skilled in the art will appreciate and understand that the various features of the drawings discussed below are not necessarily drawn to scale, and that dimensions of various features and elements of the drawings may be expanded or reduced to more clearly illustrate the features shown therein.

DETAILED DESCRIPTION

The present disclosure is directed to an instrument having soft tip and an interface formed between the soft tip and an elongated portion of the instrument. In some instances, the elongated portion may be a cannula. In some instances, the instruments may be used in procedures such as ophthalmic surgical procedures. However, the disclosure is not so limited, and the elongated portion and the interface formed therebetween may be utilized in any suitable or desired environment or purpose.

FIG. 1 shows an example instrument 10 having a soft tip 130. The instrument 10 includes an elongated portion 100 having an outer surface 107, a proximal end 101, and a distal end 105 and defining a passage 115. The passage 115 defines a wall 113 that is formed between the passage 115 and the outer surface 107. In some implementations, the elongated portion 100 may be a needle or a cannula. In other implementations, the elongated portion 100 may correspond to other types of hollow bodies for use in other types of procedures. Thus, although the balance of the description is made with reference to ophthalmic surgical procedures, the scope of the disclosure is not so limited and may be utilized in many other applications, both medical and non-medical.

The elongated portion 100 may be formed from any desired or suitable material. For example, in some instances, the elongated portion 100 may be formed from a metal such as stainless steel or titanium. However, the elongated instrument body 100 may be formed from any suitable material. For example, the elongated portion 100 may be formed from a biocompatible material, including a biocompatible polymer, metal, ceramic, or other material. In other implementations, the instrument body may be formed from silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), polybenzimidazol (PBI), rubber, latex, or other medically compatible metals, polymers, or plastic compounds.

The passage 115 may be utilized to conduct an aspiration or irrigation fluid flow. The instrument 10 also includes a soft tip 130. The soft tip 130 may be coupled at a distal end 131 of the elongated portion 100. The soft tip 130 may include an end surface 133 and may define a passage 134. Also, in some instances, a cross-sectional size of the passage 134 may be the same as a cross-sectional size of the passage 115. For example, for passages 115 and 134 having cylindrical shapes, the diameters of the passages 115 and 134 may be the same or substantially the same. In other implementations, the size and/or cross-sectional shape of the passages 115 and 134 may be different. Additionally, the passage 115 and 134 may be aligned with each other. For example, a longitudinal axis of the passages 115 and 134 may be aligned. The passages 115 and 134 define a continuous passage 170 extending through the instrument 10.

The soft tip 130 is adapted to provide a cushioning and/or non-abrasive engagement with delicate tissues or membranes, such as in a patient's eye. In some instances, the soft tip 130 may be formed from any soft material. Particularly, in some instances, the soft tip 130 may be formed from any medically compatible soft material. The soft tip 130 may be formed from materials including, for example, silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), polybenzimidazol (PBI), rubber, latex, combinations thereof, or other medically compatible polymers or plastic compounds. In some instances, the material forming the soft tip 130 may have a durometer value of 80 A. In other instances, the material forming the soft tip 130 may have a durometer value within the range of 50 A to 50 D. However, the disclosure is not so limiting. Rather, these hardness values are provided merely as examples. Thus, the material forming the soft tip 130 may have any desired hardness. In some implementations, the elongated portion and soft tip may comprise the same or similar materials.

In some instances, the elongated portion 100 may have a length within the range of approximately 20.0 mm to 40.0 mm. In other implementations, the elongated portion 100 may have a longer or shorter length. Further, the elongated portion 100 may have a gauge size between 20 and 30 gauge. Thus, for example, in some instance, the elongated portion 100 may have an outer diameter within the range of 0.30 mm to 0.40 mm. However, the scope of the disclosure is not so limited. Thus, in other implementations, the elongated portion 100 may be of any suitable or desired size. Additionally, in some instances, the passages 115 and 134 may a diameter within the range of approximately 0.30 mm to 0.01 mm. The soft tip 130 may have a length within the range of about 0.5 mm to 1.0 mm. Further, an exterior size and shape of the soft tip 130 may correspond to the size and shape of the elongated portion 100, thereby producing a smooth transition between the elongated portion 100 and the soft tip 130. For example, for an instrument 10 having a cylindrical shape, outer diameters of the elongated portion 100 and the soft tip 130 may be the same. Also, the diameters of the passages 115 and 134 may also be the same providing a continuous passage through the instrument 10.

In other implementations, the size and shapes of the elongated portion 100 and soft tip 130 may be different. For example, in some instances, the outer diameter of the elongated portion 100 may be different from the outer diameter of the soft tip 130. Thus, in some instances, a step or transition may exist at the interface between the soft tip 130 and the elongated portion 100. Further, in some instances, the soft tip 130 may have a tapered exterior surface. Thus, in some instances, the instrument 10 may include a smooth transition between the elongated portion 100 and the soft tip 130 while the soft tip 130 may taper to a smaller size at a distal end 132 thereof. Also, in some instances, the diameters of the passages 115 and 134 may be different such that there is a step or transition between the passage 115 and passage 134.

Figure 1B:
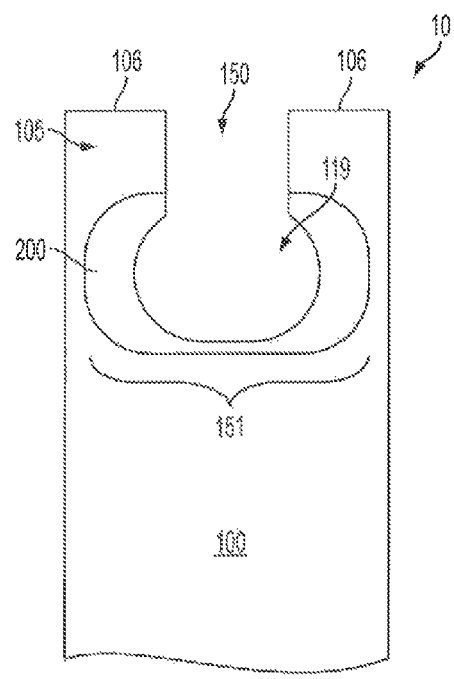

The soft tip 130 and the elongated portion 100 may include interlocking features 119, e.g., one or more interlocking tongues 120 and grooves 121. In some implementations, as shown in FIGS. 1A and 1B, the elongated portion 100 may define one or more grooves 121 formed at a distal end 105 of the elongated portion 100. Also, the soft tip 130 may define one or more tongues 120 at a proximal end 131 of the soft tip 130. The tongues 120 are received into the grooves 121 to interlockingly secure the soft tip 130 to the elongated portion 100. An engagement site 150 defines a location where the soft tip 130 and the elongated portion 100 are coupled together. The engagement site 150 may define a surface area 151 greater than a cross-sectional area of the elongated portion 100 so as to facilitate a secure and stable connection between the soft tip 130 and the elongated portion 100, even for small gauge sizes (e.g., 25 gauge or less). Further, the interlocking features provides for coupling the soft tip 130 to the elongated portion 100 while avoiding an undesirable reduction in flow rates through the passages 115, 134.

Figure 1C:
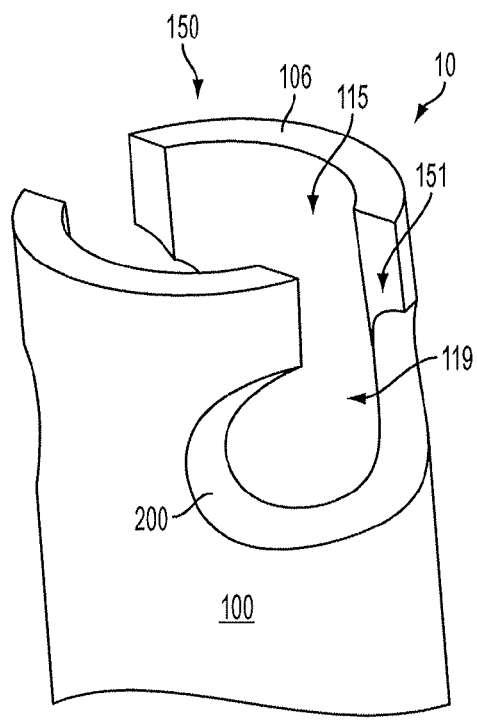
Figure 1D:
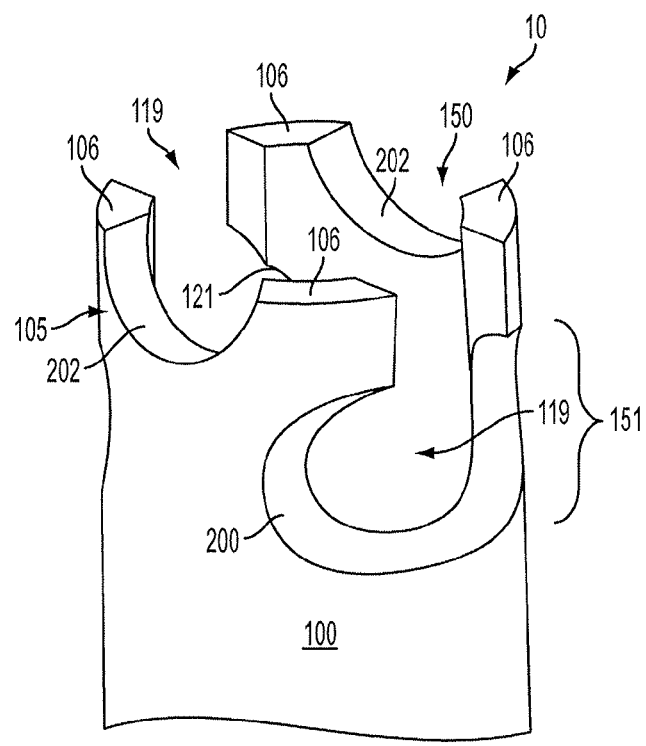

As shown in FIG. 1A, the soft tip 130 may be coupled at a circumferential edge 106 of the distal end 105 of the elongated portion 100 at the engagement site 150. As FIGS. 1B-1D illustrate, the engagement site 150 may have interlocking features 119 adapted to increase the surface area 151 at the engagement site 150 where the soft tip 130 engages the distal end 105 of the elongated portion 100. As explained above, in some instances, the surface features 119 may include one or more interlocking tongue 120 and groove 121. As illustrated in FIG. 1A, in some instances, the one or more tongues 120 of the soft tip 130 may engage and interlock with corresponding grooves 121 formed in the circumferential edge 106 of the distal end 105 of the elongated portion 100. In other instances, the elongated portion 100 may include tongues that are received in grooves formed in the soft tip 130.

The soft tip 130 and the elongated portion 100 may be coupled together utilizing numerous manufacturing methods. For example, coupling of the soft tip 130 with the elongated portion 100 may be accomplished with extrusion, casting, molding, injection molding, insert molding, welding, adhesives, or other desired or suitable methods. For example, the soft tip 130 may be formed onto the elongated portion 100 by insert molding. Moreover, the coupling may be accomplished using combinations of one or more of these methods.

FIGS. 1B-1C illustrate the distal ends 105 of example implementations of the elongated portion 100. However, as explained above, the interlocking features 119 shown in FIGS. 1B-1C may alternately be formed in the soft tip 130. As shown in FIGS. 1B-1C, the elongated portion 100 may include a plurality of grooves 200. For example, as illustrated, the elongated portion 100 may include two grooves 200. However, in other instances, any number of grooves 200 may be used. Further, the grooves 200 may be identical in shape to each other. However, in other instances, the shapes of the grooves 200 may be different from each other. In some instances, the grooves 200 may be radially offset from each other. For example, the grooves 200 may be arranged at a 180° offset about a longitudinal axis of the elongated portion 100 along the circumferential edge 106. In other instances, the grooves 200 may be arranged at different radial offsets. Moreover, elongated portions 100 or soft tips 130 having more than two grooves 200 may be offset from each other at regular intervals. In other instances, the grooves 200 may be offset from each other at irregular intervals.

Figure 2:
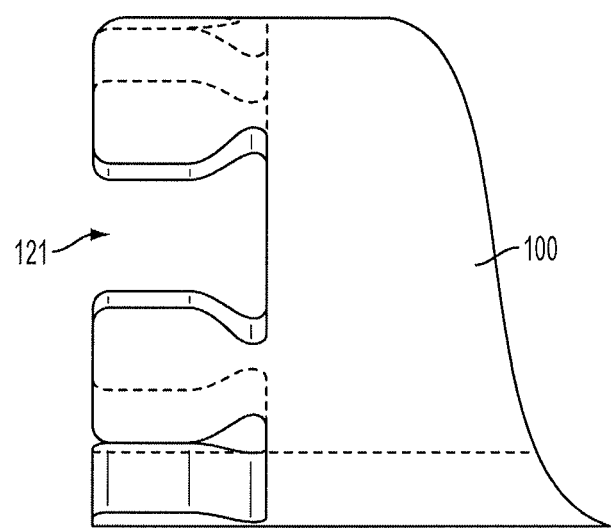
FIG. 2 is a detail view of an example instrument showing a shape of an example groove formed in the instrument.

The grooves may be formed in a variety of shapes or configurations. For example, as shown in FIG. 1A, the interlocking features 119 may include grooves 121 having a generally circular shape. Alternately, as shown in FIGS. 1B and 1C, the interlocking features 119 may include grooves 200 having a flattened circular or oval shape. Although, in other instances, the grooves 200 may have any desired shape. Still further, as shown in FIG. 1D, the interlocking features 119 may have a combination of deep grooves 200 and shallow grooves 202. The grooves 202 may be radially offset 180° from each other. In some instances, the shallow grooves 202 may be in the form of arc-shaped recesses and may be radially offset 180° from each other. Further, the set of grooves 200 may be radially offset from the set of grooves 202 by 90°. Also, the deeper grooves 200 may be generally circular or oval in shape. Thus, grooves of varying depths may be utilized. However, this configuration is used merely as an example. Any number of grooves having any number of different shapes and configurations may be used. With the grooves of one configuration or another, distal end 105 of the elongated portion 100 (or, in the case of the proximal end 131 of the soft tip 130) may have the appearance of a "jigsaw puzzle piece." Additionally, the grooves enlarge the surface area 151 of the circumferential edge 106 to provide for enhanced contact between the soft tip 130 and the elongated portion 100. FIG. 2 shows a further example of a groove 121 that may be formed. FIG. 2 shows the grooves 121 as having a generally flattened end.

Figure 3:
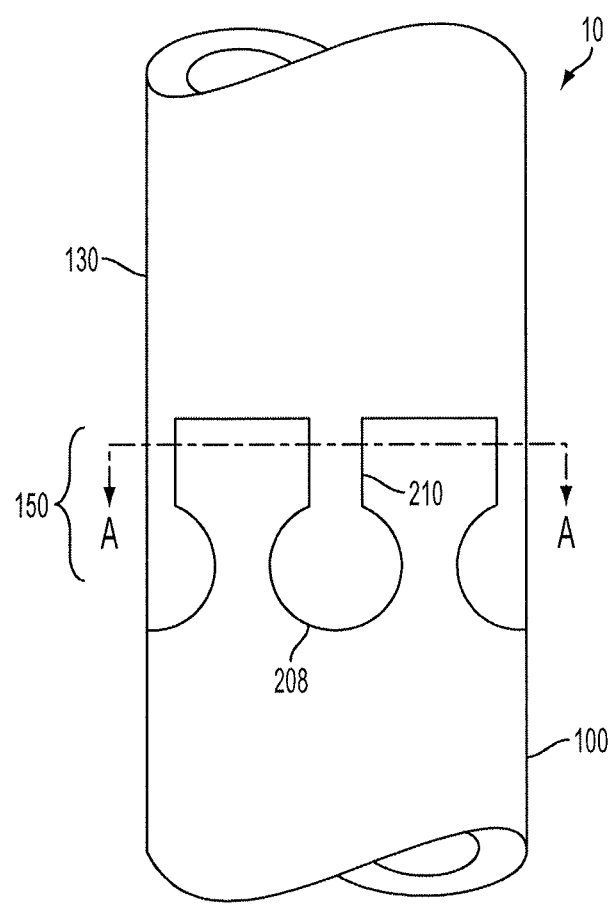
FIG. 3 shows a detail view of an engagement site of an example instrument.
Figure 4:
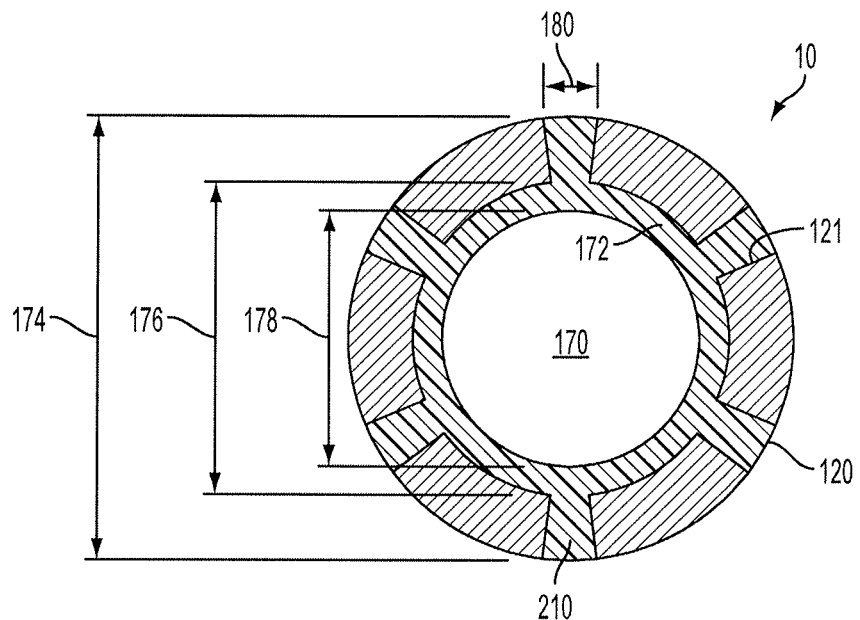
FIG. 4 is an example cross-sectional view of the instrument shown in FIG. 3.
Figure 5:
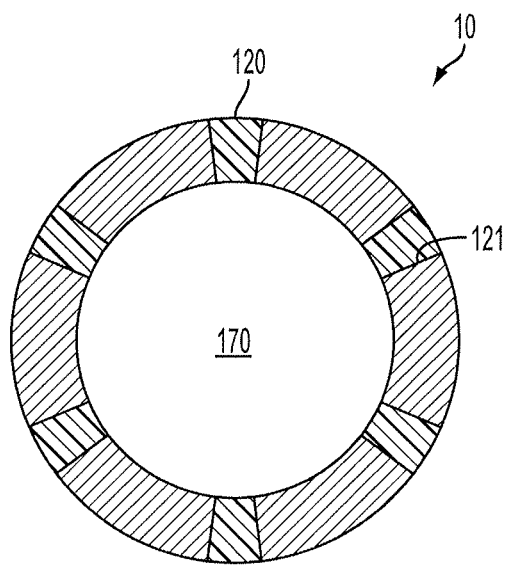
FIG. 5 is a cross-sectional view of another example instrument.

FIG. 3 shows a detail view of the engagement site 150 of an example instrument 10 according to some implementations. In the example shown, the interlocking tongues 120 and grooves 121 have an enlarged portion 208 and a reduced portion 210. FIG. 4 shows a cross-sectional view of the example instrument taken along line A-A through the reduced portion 210. Referring to FIG. 4, the example instrument 10 includes six pairs of corresponding tongues 120 and grooves 121. However, this is provided merely as an example. Thus, any number of tongues 120 and grooves 121 may be provided. As shown, in some instances, the material forming the tongues 120 may also form an annular portion 172 that overlaps a portion of the passage 170 at the engagement site 150. The annular portion 172 may reduce a cross-sectional area of the passage 170 through at least a portion of the engagement site 150. In other implementations, though, the engagement site 150 may not include an annular portion 172 within the passage 170. For example, FIG. 5 shows an example instrument 10 that does not include the annular portion 172.

Referring again to FIG. 4, the illustrated example instrument 10 may have an outer diameter 174 and an inner diameter 176. The annular portion 172 may define a diameter 178. In the case of a 27 gauge cannula, the outer diameter 174 may be 0.40 mm and the inner diameter 176 may be 0.30 mm. The diameter 178 may be within the range of 0.30 mm to 0.27 mm. Thus, in some instances, a thickness of the annular portion 172 may be within the range of 0.0 mm to 0.015 mm.

Further, the reduced portion 210 may have a thickness 180. The thickness 180 may be within the range 0.05 mm to 0.10 mm. Thus, in some instances, the ratio of the area defined by the reduced portions 210 to the entire cross-sectional area of the instrument 10 (not including the annular portion 172) may be between 14 and 27 percent. However, the particular values described above are provided merely as examples. Thus, in other instances, the thickness 180 may be any desired value. Further, although six sets of tongues 120 and grooves 121 are shown, more or fewer may be included. Also, in other instances, the ratio may be higher or smaller than the range indicated. Still further, the thickness of the annular portion 172 may be greater or smaller than the examples described above. That is, the values provided are for example purposes only and are not intended to be limiting.

Although shown as a circular cross-section, as explained herein, the scope of the disclosure is not so limited. Thus, while the examples shown in FIGS. 3 and 4 have generally circular cross-sections, the cross-sections may have any desired shape. Further, the annular portion 172 may conform to the cross-sectional shape of the instrument such that the diameter 178 also substantially corresponds to the cross-sectional shape of the instrument 10 or may be defined to be any other shape. Thus, in some instances where the instrument 10 has a non-circular cross-sectional shape, the diameter 178 may still be defined to be circular. However, in still other instances, the diameter 178 may be defined to be any desired shape.

The various types of grooves or tongues may be formed in or about the distal end of the elongated portion 100 in any desired manner. For example, the grooves and/or tongues may be formed by laser cutting, water jet cutting, milling, drilling, electron discharge machining, chemical etching, electrolytic etching, or any other suitable method. The interlocking features 119 are designed to increase and/or enhance the cross-sectional surface area, e.g., surface area 151, at the engagement site 150 to facilitate attachment of the soft tip 130 to the elongated portion 100.

FIG. 6 shows an instrument 10' according to an alternative implementation. The instrument 10' includes an elongated portion 100 having a proximal end 101 and a distal end 105 and defining a flow passage 115 therethrough. The soft tip 130 includes a passage 134. The passages 115 and 130 may be similar to those explained above. The distal end 105 of the elongated portion 100 includes an enhanced surface 135 to enhance coupling of the soft tip 130 and the elongated portion 100. In some instances, the enhanced surface 135 may contain a network of pores or voids that are adapted to receive material forming the soft tip 130, thereby enhancing bond between the soft tip 130 and the elongate portion 100. In other instances, the enhanced surface 135 may be a roughened surface to increase a surface area to enhance bonding between the soft tip 130 and the elongated portion 100. In some implementations, the enhanced surface 135 may be formed with the use of urea. Further, in some instances, the enhanced surface 135 may be both porous and roughened. In still other implementations, the enhanced surface 135 may include other features, either alone or in combination with one or more of the features described herein to enhance bonding.

The distal end 105 of the elongated portion 100 may also be treated to enhance adhesion of the material forming the soft tip 130. For example, a plasma treatment may be applied to the distal end 105. The plasma treatment may clean, etch, and alter the chemistry of the material forming the elongated portion 100 to promote coupling of the soft tip 130 thereto. Further, a silicate layer may be formed at the distal end 105 of the elongated portion 100 to enhance adhesion of the soft tip 130 to the elongated portion 100.

The soft tip 130 may be molded, extruded onto, or adhered to the enhanced surface 135. The enhanced surface 135 may include one or more of pores, passages, or a texture that defines additional surface area at the engagement site 150 for interaction with the soft tip 130. Similarly, the soft tip 130 may include a surface that engages the enhanced surface 135 to form a bond between the soft tip 130 and elongated portion 100. The additional or enhanced surface area provided by the enhanced surface 135 facilitates the engagement between and adherence of the soft tip 130 to the elongated portion 100. In some instances, adherence between the soft tip 130 and the elongated portion 100 may be obtained by application of an adhesive that can flow into the surface features of the enhanced surface 135 and the corresponding surface of the soft tip 130 to enhance the adhesion therebetween. Alternatively, the soft tip 130 may be extruded or molded directly onto the enhanced surface 135 of the elongated portion 100, such as, for example, by insert molding. The material forming the soft tip 130, such as a plastic or elastomeric material, is then able to flow into the surface features (e.g., pores, cracks and/or passages) of the enhanced surface 135.

FIGS. 7A-7B illustrate another example instrument 10". The soft tip 130 of instrument 10" is connected at the distal end 105 of the elongated portion 100 via interlocking features 119 in combination with a enhanced surface 135 similar to the enhanced surface 135 described above. The enhanced surface 135 may be formed along an interior surface of one or more of the grooves 121. Alternately or in addition, one or more locations of the enhanced surface 135 may be provided along the circumferential edge 106. In other implementations, the enhanced surface 135 may be provided along the entire circumferential edge 106. As shown, the instrument 10" includes six grooves 121, but any number of grooves 121 may be used. Thus, the soft tip 130 may be coupled to the elongated portion 100 via both interlocking provided by the mating tongues 120 and grooves 121 as well as the increased surface area provided by the enhanced surface 135. Again, while the grooves 121 are shown as being formed in the elongated portion 100, the grooves 121 may be formed in the soft tip 130 while the tongues 120 may be formed in the elongated portion 100.

Figure 8:
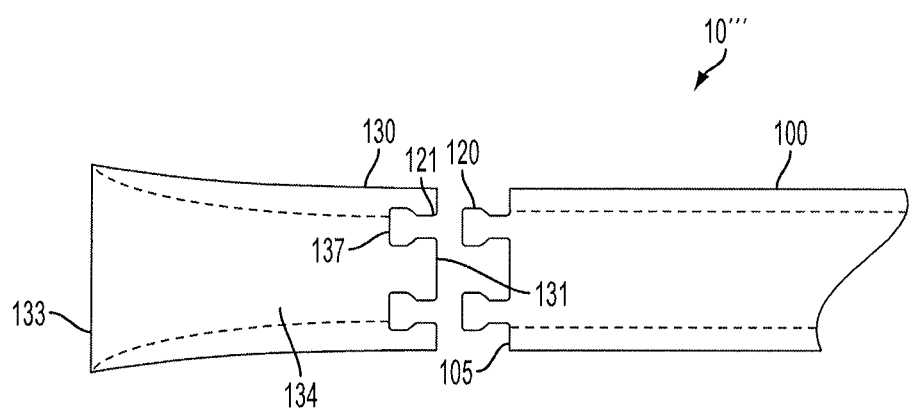
FIG. 8 is a partial detail view of another example instrument in an exploded configuration.

FIG. 8 illustrates another example instrument 10'''. The instrument 10''' includes a soft tip 130 having a circumferential edge 133 that is outwardly flared at distal end 132. In some instances, the soft tip 130 may be tapered all or a portion of its length from the flared circumferential edge 133 to a reduced cross-sectional size. For example, in some instances, the soft tip 130 may taper from an outer profile corresponding to that of the elongated portion 100 to an enlarged circumferential edge 133. Further, in some instances, the passage 134 may be tapered.

FIG. 8 also shows the distal end 105 of the elongated portion 100, with tongues 120 formed in the elongated portion 100 rather than the soft tip 130. The soft tip 130 may include one or more corresponding grooves 121 that are adapted to receive in the tongues 120 formed in the elongated portion 100. In some implementations, the grooves 121 may have an enlarged head 137. Similarly, the tongues 120 may have a shape complementary to the shape of the grooves 121 such that the tongues 120 are matingly received into the grooves 121. The grooves 121 and tongues 120 provide for an interlocking engagement. Further, the enlarged head 137 of the grooves 121 provides an enlarged perimeter and, hence, contact area at which the soft tip 130 and the elongated portion 100 engage each other. Consequently, the interlocking tongues 120 and grooves 121 provide for an improved connection between the soft tip 130 and the elongated portion 100 of the instrument 10'''.

Figure 9:
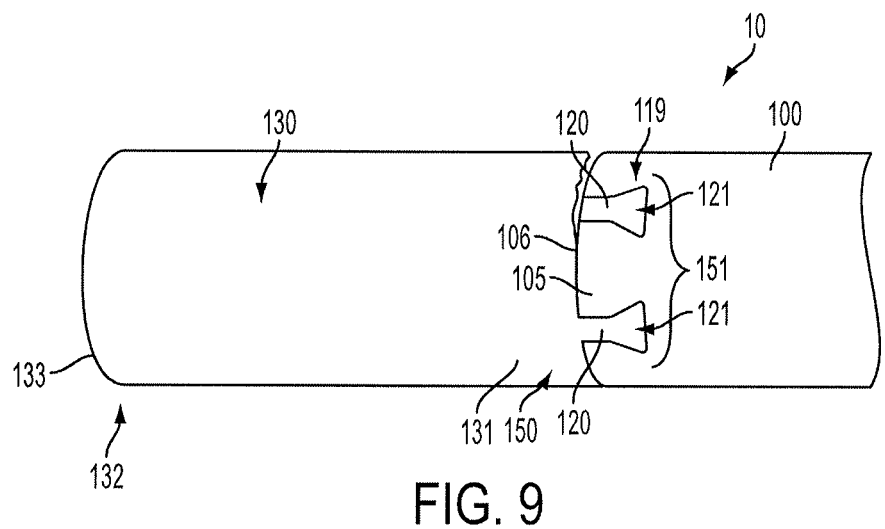
FIG. 9 is a detail view of the interface of the soft tip and the elongated portion of an example instrument illustrating partial separation of the soft tip from the elongated portion.

FIG. 9 is a detail view of an example instrument 10 in which two of the grooves 121 and corresponding tongues 120 are shown. The soft tip 130 may be formed from silicone or other material. For example, the soft tip 130 may be formed from one or more of the materials identified above. Further, the soft tip 130 may be molded directly onto the elongated portion 100.

In one or more of the examples described herein, the grooves 120 formed in the distal end 105 of the elongated portion 100 may be formed by laser cutting. Similarly, for implementations in which the tongues 120 are formed at the distal end 105 of the elongated portion 100, the tongues 120 may be formed via laser cutting. However, other manufacturing methods may be utilized to form the tongues 120 or grooves 121 in the elongated portion 100. For example, other machining methods may be used. Thus, any suitable manufacturing operation may be used to form the grooves 121 or tongues 120.

In some instances, when coupling the soft tip 130 to the elongated portion 100, the instrument body may be placed in an injection mold defining a cavity adapted to form the soft tip 130. A portion of the elongated portion 100, such as the distal end 105, may extend into the cavity. Silicon or other suitable or desired material may be injected into the cavity forming the soft tip 130. The injected material flows into the grooves 121 formed in the distal end 105 of the elongated portion 100 or, alternately, around the tongues 120 formed at the distal end 105 to form the corresponding interlocking features. Further, the injected materials also fills in surface features of the elongated portion 100, such as the surface features of the perimeter defined at the distal end 105 by the grooves 121 or tongues 120 to further enhance the mechanical bond formed between the elongated portion 100 and the soft tip 130.

FIG. 9 shows the soft tip 130 partially separated from the elongated portion 100. For example, FIG. 9 may illustrate a condition in which the soft tip 130 has been partially torn away from the elongated portion 100. In some instances, separation of the soft tip 130 from the elongated portion 100 may result in the interlocking feature of the soft tip 130 remaining with the elongated portion 100. For example, as shown in FIG. 9, upon partial or complete separation of the soft tip 130 from the elongated portion, the tongues 120 formed at a proximal end 131 of the soft tip 130 may remain within the corresponding groove 121 and, hence, coupled to the elongated portion 100. Moreover, because the tongues 120 remain retained within the corresponding groove 121, the instrument 10 is less likely to become occluded by debris from the soft tip 130. That is, if the soft tip 130 were to become partially or completely separated from the elongated portion 100, the interlocking relationship between the tongues 120 and grooves 121 work to retain the tongues 120 of the soft tip 130, thereby preventing occlusion of the instrument 10 by the separated tongues 120. As a result, risk to a patient is reduced.

A further benefit is that the passage 134 may be the same size as the passage 115 formed in the elongated portion. This improves the flow capacity passing through the instruments as well as reducing the risk of occlusion within the soft tip 130. Further, the engagement of the soft tip 130 and the elongated portion 100 includes a surface area defined by the profile of the grooves 121 and tongues 120 that exceeds a surface area associated with a transverse cross-sectional area. Thus, the interlocking features of soft tip 130 and elongated portion 100 provide both mechanical interlocking and an increase in the surface area available for coupling while providing a lumen through the instrument having a continuous cross-sectional shape. Adhesives may also be used to augment coupling between the soft tip 130 and elongated portion 100 interlocking connection. Still further, in some implementations, the soft tip 130 and passage 134 formed therethrough may be tapered and a distal end 132 of the soft tip 130 may be flared to improve fluid flow characteristics through the instrument.

Figure 10:
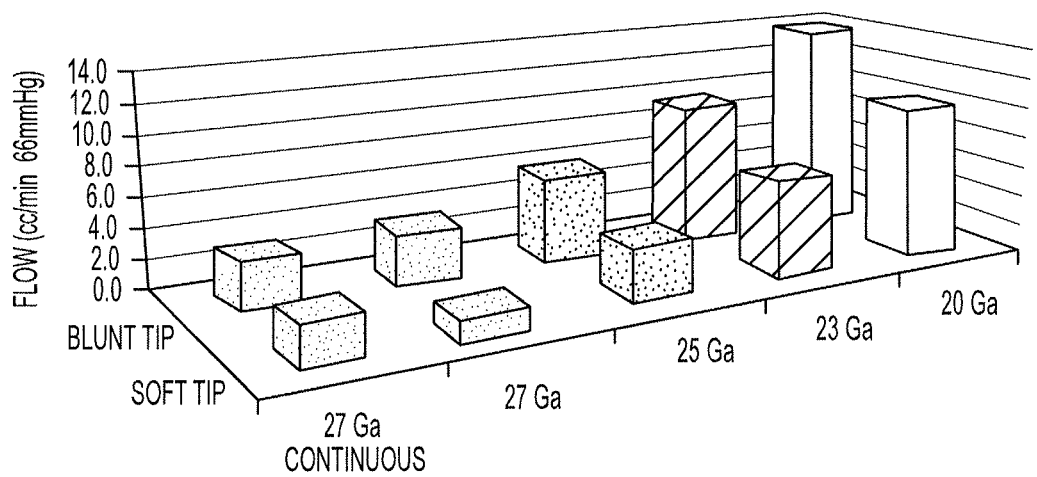
FIG. 10 is a graphical illustration of passive flow characteristics of different sized instruments with and without a soft tip.

FIG. 10 illustrates passive flow characteristics through cannulas of a defined size. FIG. 10 also illustrates the passive flow characteristics of cannulas having a blunt tip as well as cannulas having a soft tip. Particularly, FIG. 10 displays measured passive flow data of cannulas having various diameters (e.g., 20 to 27 gauge). The passive flow data (in cm$^3$/min.) represented in FIG. 10 were collected from experiments performed at a pressure of 66 mm of Hg (i.e., 1.28 psi or 0.88 bar). The passive flow data graphically illustrated in FIG. 10 are shown below in Table 1.

Figure 11:
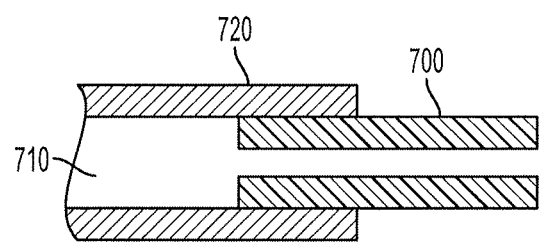
FIG. 11 shows a distal end of a soft tip cannula.

Table 1 includes flow rate data for passive flow through cannulas of the indicated types. For each indicated gauge size, Table 1 includes flow data of both a blunt tip cannula (i.e., a cannula that lacks a soft tip) and a cannula including a soft tip. For the 20, 23, 25, and 27 gauge cannulas identified with a single asterisk (*), a soft tip 700 is received into passage 710 of cannula 720, as shown in FIG. 11.

The last entry in Table 1 identified with two asterisks (**) includes data for both a blunt tip cannula and a soft tip cannula. The soft tip cannula is coupled to the cannula as described herein. Particularly, the soft tip is coupled to an end of the cannula via insert molding, although any of the methods described herein may be used. Further, for the example presented in Table 1, the passage of the soft tip and the passage of the cannula are aligned and are substantially the same in shape and size.

The data are based upon a pressure differential across the cannula (and soft tip where applicable) of 66 mm of Hg. The flow rates indicated are measurements resulting from this pressure differential.

TABLE 1

Backflush Passive Flow Characteristics for Blunt and Soft Tip Cannulas

| Gauge | Blunt Tip (cm$^3$/min.) | Soft Tip (cm$^3$/min.) | Percentage (%) of flow through Soft Tip vs. Blunt Tip |
|---|---|---|---|
| 20* | 14.0 | 10.2 | 72.9 |
| 23* | 9.5 | 6.6 | 69.5 |
| 25* | 6.0 | 3.9 | 65.0 |
| 27* | 3.4 | 1.5 | 44.1 |
| 27** | 3.6 | 3.1 | 86.1 |

*Soft tip received within passage of cannula
**Soft tip formed by insert molding according to the present disclosure Referring to the 27* gauge cannula, the flow rate through the cannula having the soft tip is approximately 44% of the flow through the corresponding blunt tip cannula. That is, the soft tip cannula of the 27* gauge variety is approximately 56% less than the flow rate through the blunt tip variety. Conversely, the soft tip cannula of the 27 gauge variety has approximately 86% of flow rate of the blunt tip variety. That is, the cannula with the soft tip has only a 14% reduction in flow rate compared to the blunt tip. Further, the 3.1 cc/min. flow rate of the 27 gauge soft tip cannula is approximately 107% of the 1.5 cc/min. flow rate of the 27* gauge soft tip cannula. FIG. 10 shows the data presented in Table 1 in a graphical representation. In FIG. 10, the data identified by "27 Ga Continuous" corresponds to the 27** gauge data presented in Table 1.

In some implementations, the elongated portion may be any gauge cannula. For example, in some instances, the elongated portion may have a gauge size within the range of 7 to 32. Thus, in some instances, the elongated portion may have a lumen with an inner diameter between 0.150 in (3.810 mm) to 0.00325 in (0.0826 mm). In some implementations, the elongated portion may have a gauge size of 25 gauge or less. Particularly, in some instances, the elongated portion may have a gauge size within the range of 25 to 32 gauge.

It should be understood that, although many aspects have been described herein, some implementations may include all of the features, others may include some features while including other, different features, and in still other instances, other implementations may omit some features while including others. That is, various implementations may include one, some, or all of the features described herein. It will be understood by those skilled in the art that various changes and modifications can be made without departing from the spirit and scope of the disclosure, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described examples. Accordingly, various features and characteristics as discussed herein may be selectively interchanged and applied to other illustrated and non-illustrated example implementations, and numerous variations, modifications, and additions further can be made thereto without departing from the spirit and scope of the present disclosure as set forth in the appended claims.

What is claimed is:

1. A medical instrument for ophthalmic procedures comprising:
   an elongated portion comprising:
   a distal end;
   a first inner surface that forms a first lumen extending throughout the elongated portion;

an outer surface;
a wall formed between the outer surface and the first lumen; and
a plurality of longitudinally extending grooves formed in the wall and extending from the distal end, an entirety of the grooves extending through an entire thickness of the wall from the outer surface to the first passage; and
a tip interlocked with the distal end of the elongated portion at an engagement site, the tip comprising:
a second inner surface that forms a second lumen extending throughout the tip;
a plurality of longitudinally extending tongues extending from a proximal end of the tip and received into the longitudinally extending grooves, each of the longitudinally extending tongues comprising:
a first portion extending from the distal end of the elongated portion; and
a second portion that is oval, or flared, the second portion adjoining the first portion at a distal end of the first portion, a width of the second portion is greater than a width of the distal end of the first portion, and a combined cross-sectional area of the first portions of the tongues is 14 to 27 percent of a cross-sectional area of the elongate portion; and
a distal end formed from an elastomeric material with a durometer value of 50A to 80A for preventing damage during contact with a patient's eye, wherein the distal end of the tip defines a distal end of the medical instrument;
wherein the elongated portion and the tip have a diameter that is smaller than a gauge size of 25, the grooves are interlockingly attached with and shaped complementarily to the tongues forming a continuous inner surface consisting of the first lumen and the second lumen, the continuous inner surface having a single constant diameter continuously throughout the elongated portion and the tip.

2. The medical instrument of claim 1, wherein the engagement site comprises a network of pores, a network of voids, or a roughened surface.

3. The medical instrument of claim 1, wherein the tip is molded to the engagement site.

4. The medical instrument of claim 1, wherein the elongated portion comprises a cannula.

5. The medical instrument of claim 1, wherein the distal end of the tip is outwardly flared.

6. The medical instrument of claim 1, wherein the elongated portion has a hardness that is higher than the durometer value of the elastomeric material.

7. The medical instrument of claim 1, wherein at least a portion of the tip is silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), polybenzimidazol (PBI), rubber, latex, combinations thereof, or other polymer or plastic compounds.

8. The instrument of claim 1, wherein the tip further comprises a constant outer diameter.

* * * * *